United States Patent
Lechot

(10) Patent No.: US 6,540,739 B2
(45) Date of Patent: *Apr. 1, 2003

(54) SURGICAL INSTRUMENTATION SYSTEM

(75) Inventor: Andre Lechot, Orvin (CH)

(73) Assignee: Precimed, S.A., Orvin (CH)

( * ) Notice: Subject to any disclaimer, the term of this patent is extended or adjusted under 35 U.S.C. 154(b) by 24 days.

This patent is subject to a terminal disclaimer.

(21) Appl. No.: 09/902,369

(22) Filed: Jul. 9, 2001

(65) Prior Publication Data

US 2002/0002365 A1 Jan. 3, 2002

Related U.S. Application Data

(63) Continuation of application No. 09/602,341, filed on Jun. 24, 2000, now Pat. No. 6,264,647.

(51) Int. Cl.[7] ............................................... A61B 17/00
(52) U.S. Cl. ................. 606/1; 606/80; 606/81
(58) Field of Search ................. 606/1, 79, 80, 606/81

(56) References Cited

U.S. PATENT DOCUMENTS

| 5,236,433 A | * | 8/1993 | Salyer | 606/80 |
| 5,562,655 A | * | 10/1996 | Mittelstadt et al. | 606/1 |
| 5,582,607 A | * | 12/1996 | Lackman | 606/1 |
| 5,658,290 A | * | 8/1997 | Lechot | 606/80 |
| 6,093,184 A | * | 7/2000 | Campbell et al. | 606/1 |
| 6,409,732 B1 | * | 6/2002 | Salyer | 606/91 |

* cited by examiner

Primary Examiner—Linda C. M. Dvorak
Assistant Examiner—Jocelyn Ram
(74) Attorney, Agent, or Firm—John L. Chiatalas

(57) ABSTRACT

Instrument holder comprising a shank (1) equipped with a head (2) designed to receive an instrument and a locking component (4) pushed against the head by a spring (9) bearing on a ring (11) sliding on the shank, and having means of connection (8, 12) on the shank which is engaged by rotation of the ring, in such a way that the release of the ring allows the locking component, the spring and the ring to slide freely in order to permit cleaning of the instrument holder.

40 Claims, 1 Drawing Sheet

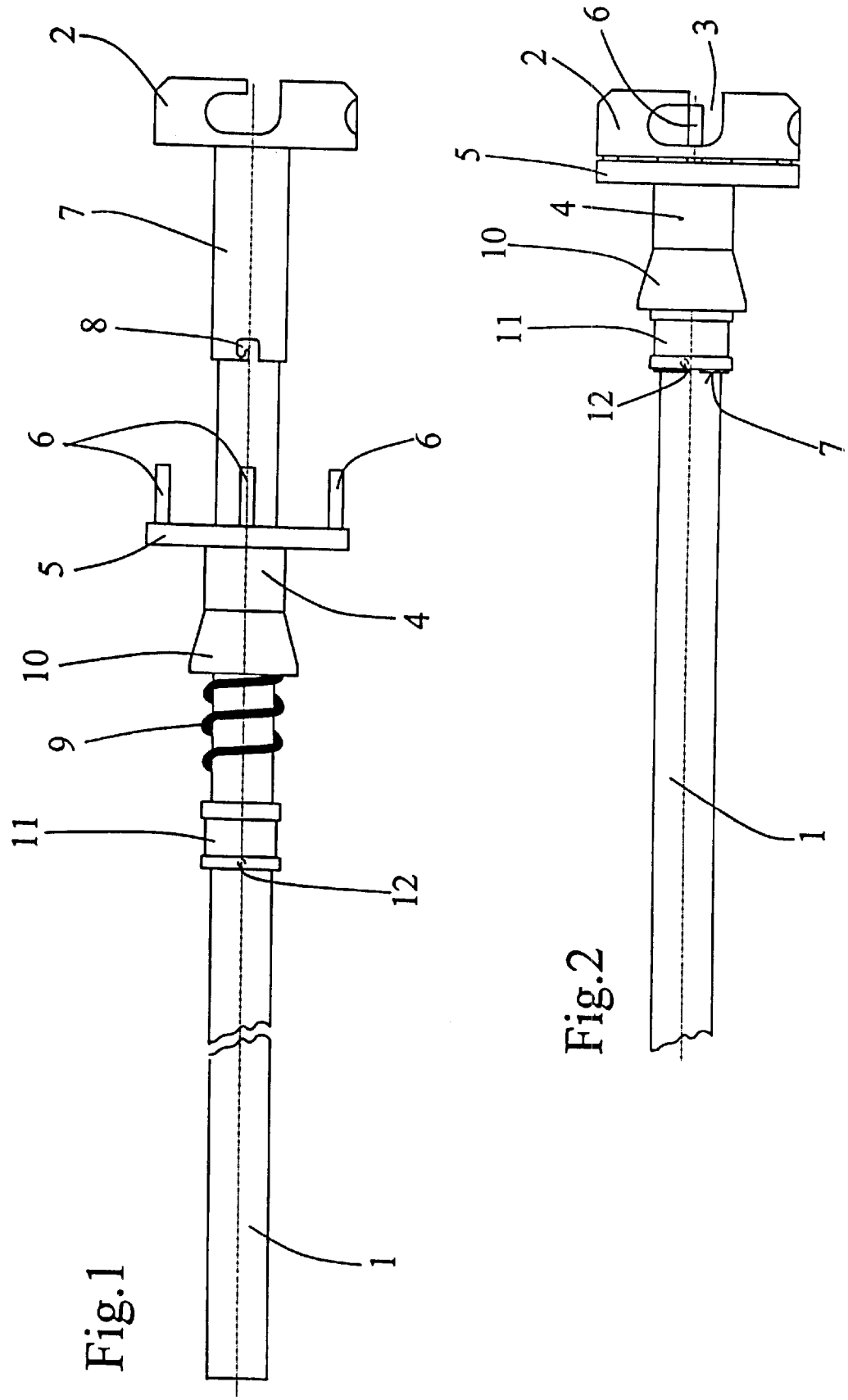

SURGICAL INSTRUMENTATION SYSTEM

"This application is a continuation of the present inventor's co-pending application Ser. No. 09/602,341, filed Jun. 24, 2000 and entitled, Instrument Holder for Surgical Instrument, now U.S. Pat. No. 6,264,647."

BACKGROUND OF THE INVENTION

The invention relates to an instrument holder for a surgical instrument, comprising a shank equipped with a head designed to receive an instrument, and an annular locking component mounted so as to slide about the shank, under the head, equipped with locking means which cooperate with the head so as to lock the instrument on the head, and pushed against the head by a helical spring.

An instrument holder of this type is known in particular from U.S. Pat. Nos. 5,658,290 and 5,236,433, the contents of which are incorporated by reference.

A surgical instrument, for example for preparing for the fitting of a hip prosthesis, works in a medium which causes considerable soiling of the instrument and the instrument holder. Moreover, a surgical instrument holder must be cleaned very frequently and very carefully in order to avoid any risk of infection. However, cleaning of surgical instruments is difficult, in particular cleaning of the space between the shank and the locking component on account of the presence of bone debris and coagulated blood.

SUMMARY OF THE INVENTION

The object of the invention is to provide optimum conditions for rapid cleaning.

To this end, the instrument holder according to the invention is distinguished by the fact that the thrust spring bears on a ring sliding on the shank, and that the shank and the ring have means of connection set in use manually by rotation of the ring, in such a way that the release of the ring allows the locking component, the spring and the ring to slide freely on the shank. This almost instantaneous disassembly of the component parts of the instrument holder allows it to be thoroughly and quickly cleaned.

According to a preferred embodiment of the invention, the shank has, under the head, a section with a diameter greater than the diameter of the rest of the shank, on which section the ring is fixed by a bayonet fastening.

The play of the components making up the locking means on the shank permits good cleaning without it being necessary to remove these components from the shank, which avoids the risk of losing a component or mixing them up, and it obviates the need to fit the components back on the shank. The fastening and release of the ring take place instantaneously, which represents a saving in time. This makes it possible to ensure that a complete kit of instruments is not rendered unusable because of a single component being inoperative.

The head and the fastening and locking means of the instrument can be designed in many ways. These means do not form part of the actual invention.

BRIEF DESCRIPTION OF THE DRAWINGS

The attached drawing shows an embodiment of the invention by way of example.

FIG. 1 shows the instrument holder in the disassembled position.

FIG. 2 shows the instrument holder in the locked position.

DETAILED DESCRIPTION OF THE PREFERRED EMBODIMENT(S)

The instrument holder shown comprises a cylindrical shank 1, at one end of which a head 2 is fixed which is identical to the head described in U.S. Pat. No. 5,658,290, the content of which is incorporated by reference. This head has a central recess, the head forming a crown around this recess. This crown has four bayonet catches 3 diametrically opposite in pairs. A reamer analogous to the reamer shown and described in U.S. Pat. No. 5,658,290 is fixed in these catches 3. The reamer is locked in the catches 3 by an annular locking component 4 equipped with a plate 5 having four parallel fingers 6 which pass through the head 2 in order to close the bayonet catches 3, as is described in U.S. Pat. No. 5,658,290.

The locking component 4 does not slide directly on the section of the shank seen in FIG. 1, but on a section 7 with a greater diameter than the diameter of the rest of the shank. This section 7 can consist of a tubular component arranged on the shank 1. At least one bayonet catch 8 is formed at the end of the section 7 remote from the head 2. These catches are preferably at least two in number and diametrically opposed to facilitate assembly, as will be seen below. Also arranged around this section 7 there is a helical spring 9 which engages in a frustoconical widened part 10 of the locking component 4 and bears against this locking component, the median part of which slides freely on the section 7. The instrument holder is completed by a ring 11 which also slides on the section 7 and is equipped internally with a radial stud 12, that is oriented in the direction of the shank 1.

Starting from the disassembled position shown in FIG. 1, and in order to assemble the instrument holder, the locking component 4 is brought under the head 2, engaging its locking fingers 6 through the head, then, with the ring 11, the spring 9 is pushed against the locking component 4 and this spring is compressed, at the same time turning the ring 11 to the left until its stud 12 engages in the bayonet catch 8, respectively in one of the bayonet catches, in which it fastens by holding the ring 11 which is pushed rearward by the spring 9. The instrument holder can then be used as is described in U.S. Pat. No. 5,658,290. The frustoconical widened part 10 gives a grip for the thumb and index finger for pulling the locking component 4 back counter to the action of the spring 9 in order to release the instrument fixed on the instrument holder.

Conversely, in order to disassemble the instrument holder, it suffices to push the ring 11 forward counter to the action of the spring 9 and to turn it in the direction of the hands of a watch in such a way that its stud 12 is pushed out of the bayonet catch 8 by the spring 9.

It will be seen that assembly and disassembly of the instrument holder are effected instantaneously and can be done using one hand.

As is shown in FIG. 1, the shank 1 allows the components 4, 9 and 11 to be removed totally from the shank. Given the substantial play of the components 4 and 11 on the shank 1, such complete disassembly is not necessary for cleaning purposes. It is therefore possible to provide an abutment at the end of the shank in order to hold the components on the shank.

The end of the shank remote from the head 2 is shown as being cylindrical, but it can have another shape, in particular a hexagonal cross section for fastening the instrument holder on the means for driving the instrument holder in rotation.

The ring 11 could be made integral with the shank by screwing, that is to say having a screw thread in the ring and on the part 7.

The head 2 and the fingers 6 are only one example from all the possible means for connection of an instrument.

Although illustrative embodiments of the invention have been shown and described a wide range of modification, change and substitution is contemplated in the foregoing disclosure and in some instances, some features of the present invention may be employed without a corresponding use of the other features. Accordingly, it is appropriate that the appended claims be construed broadly and in a manner consistent with the scope of the invention.

What is claimed:

1. An instrument holder for a surgical instrument comprising:
   a shank with a head,
   an annular locking component slidably mounted along the shank underneath the head, cooperating with the head to lock the instrument on the holder,
   a thrust bearing member releasably mounted on the shank, under the locking component,
   a helical spring located between the locking component and the thrust bearing member,
      wherein release of the thrust bearing member allows for disassembly.

2. A The holder of claim 1, the shank further comprising a section located under the head, the section having a diameter greater than the diameter of the rest of the shank.

3. The holder of claim 1, the annular locking component having a plurality of fingers extending through the head to form bayonet catches for locking the instrument on the head.

4. The holder of claim 1 wherein the thrust bearing member is a ring.

5. The holder of claim 4 wherein the ring is slidably coupled to the shank.

6. The holder of claim 5 wherein the ring is threadedly coupled to the shank.

7. The holder of claim 4 wherein the shank has a section on which the ring is fixed by a bayonet fastening.

8. The holder of claim 7 further comprising a stud located on the ring, the stud engaging the bayonet fastening as the ring is turned to assemble the holder for use.

9. The holder of claim 4 wherein the spring is pre-compressed between the ring and the locking component.

10. The holder of claim 1 wherein the head further comprises a bayonet catch adapted to respectively receive linearly opposed radial arms from the cutting instrument, to lock the instrument on the head.

11. The holder of claim 1 wherein the thrust bearing member is mounted on the shank by a releasable stud.

12. The holder of claim 1 wherein the spring is pre-compressed between the thrust bearing member and the locking component.

13. The kit of claim 1 wherein the thrust bearing member is a ring.

14. The kit of claim 13 wherein the ring is slidably coupled to the shank.

15. The kit of claim 13 wherein the ring is threadedly coupled to the shank.

16. The kit of claim 13 wherein the shank has a section on which the ring is fixed by a bayonet fastening.

17. The kit of claim 13 wherein the spring is pre-compressed between the ring and the locking component.

18. A surgical instrumentation kit comprising:
   a plurality of cutting instruments each having a substantially hollow body defining a shape with domed outer and inner surfaces and a circumferential rim delimiting a base plane with a central axis, each instrument having a plurality of arms extending in a radial direction from the central axis to respective portions of the rim; and
   an instrument holder operative with a source of rotary power for driving a selected one of the instruments, the holder including
      a shank with a head,
      an annular locking component slidably mounted along the shank underneath the head, cooperating with the head to form a catch that locks with the arms of the instrument,
      a thrust bearing member releasably mounted on the shank, under the locking component,
         a helical spring located between the locking component and the thrust bearing member, wherein release of the thrust bearing member allows for disassembly.

19. The kit of claim 18, the shank further comprising a section located under the head, the section having a diameter greater than the diameter of the rest of the shank.

20. The kit of claim 18, the annular locking component having a plurality of fingers extending through the head to form a plurality of catches.

21. The kit of claim 18 wherein the arms of each cutting instrument respectively extend in linearly opposed radial directions from the central axis.

22. The kit of claim 18 wherein the thrust bearing member is mounted on the shank by a releasable stud.

23. The kit of claim 22 wherein the stud is located on the ring and engages a bayonet fastening located on the shank, as the ring is turned to secure the assembly together.

24. The kit of claim 18 wherein the spring is pre-compressed between the thrust bearing member and the locking component.

25. A method of preparing a surgical instrument holder for use and cleaning of debris, the holder having a shank with a head, a helical spring and an annular locking component, the method comprising the steps of:
   (a) preparing the holder for use by
      (i) sliding the annular locking component along the shank underneath the head;
      (ii) positioning the spring under the locking component;
      (iii) moving a thrust bearing member along the shank to thrust the spring against the locking component and urge it against the head, then releasably connecting the thrust bearing member to the shank to completely assemble the holder for use; and
   (b) disassembling the holder for cleaning by
      (i) releasing the thrust bearing member then
      (ii) sliding the thrust bearing member down the shank and cleaning the surgical debris.

26. The method of claim 25 wherein step (a)(iii) wherein the thrust bearing member is a ring that is slidably mounted along the shank.

27. The method of claim 26 wherein step (b)(ii) further comprises sliding the ring, spring and annular locking component down the shank.

28. The method of claim 26 wherein step (b)(ii) further comprises removing the ring, spring and annular locking component from the shank.

29. The method of claim 25 wherein step (b)(ii) further comprises partially disassembling the thrust bearing member, spring and locking component to allow cleaning of debris.

30. A method of cleaning debris from a surgical holder of the type having a shank with a head, a helical spring and an annular locking component slidably mounted on the shank between the head and the spring, the method comprising the steps of:

(a) releasing a thrust bearing member located underneath the helical spring; and (b) sliding the thrust bearing member down the shank and cleaning the surgical debris.

31. An instrument holder for an acetabular reaming instrument comprising:

shank with a head;

an annular locking component, slidably mounted along the shank underneath the head and including a plurality of fingers extending through the head to form a catch that locks the instrument on the holder;

a thrust bearing member releasably mounted by a bayonet fastening on the shank, under the locking component;

a helical spring located between the locking component and the thrust bearing member, wherein release of the thrust bearing member allows for disassembly.

32. The holder of claim 31 wherein the thrust-bearing member is a ring.

33. The holder of claim 32 wherein the ring is slidably or threadedly coupled to the shank.

34. The holder of claim 31 wherein the catch is adapted to receive a radial arm from the instrument, to lock the instrument on the head.

35. An acetabular reaming kit comprising:

a plurality of cutting instruments, each instrument having a substantially hollow body defining a shape adapted to form an acetabular cavity in bone, with domed outer and inner surfaces and a circumferential rim delimiting a base plane with a central axis, each instrument having a plurality of arms extending in a radial direction from the central axis to respective portions of the rim; and an instrument holder operative with a source of rotary power for driving a selected one of the instruments to form the acetabular cavity, the holder including a shank with a head and a bayonet fastening, an annular locking component slidably mounted along the shank underneath the head, cooperating with the head to form a plurality of catches that lock with the arms of the instrument, a thrust bearing member releasably mounted on the shank, under the locking component, by the bayonet fastening, a helical spring located between the locking component and the thrust bearing member, wherein release of the thrust bearing member allows for disassembly.

36. The kit of claim 35, the annular locking component having a plurality of fingers extending through the head to form the catch.

37. The kit of claim 36 wherein the thrust-bearing member is a ring.

38. The kit of claim 37 wherein the ring is slidably or threadedly coupled to the shank.

39. The kit of claim 35 wherein the arms of each cutting instrument respectively extend in linearly opposed radial directions from the central axis.

40. A method of preparing an acetabular reamer holder for use and cleaning of surgical debris, the holder being an assembly having a shank with a head, a helical spring and an annular locking component for grasping an instrument held by the assembly, the method comprising the steps of:

(a) assembling the holder for use by (i) sliding the annular locking component along the shank;

(ii) engaging a catch, formed by the head and locking component, to securely grasp the instrument;

(iii) sliding a ring along the shank, under the locking component, to thrust the spring against the locking component and urge it against the head;

(vi) releasably connecting the ring and shank together by engaging a bayonet fastening mechanism on the ring and shank, thus completing the assembly for use; then (b) disassembling the holder assembly by releasing the bayonet fastening mechanism, sliding the ring down the shank and cleaning the surgical debris.

* * * * *